(12) United States Patent
Ouyang et al.

(10) Patent No.: US 11,071,442 B2
(45) Date of Patent: Jul. 27, 2021

(54) PORTABLE ENDOSCOPE WITH SIDE-MOUNTABLE DISPOSABLE PORTION

(71) Applicant: UroViu Corp., Bellevue, WA (US)

(72) Inventors: Xiaolong Ouyang, Bellevue, WA (US); Robert K Deckman, Bellevue, WA (US); Shih-Ping Wang, Los Altos, CA (US)

(73) Assignee: UroViu Corp., Bellevue, WA (US)

( * ) Notice: Subject to any disclaimer, the term of this patent is extended or adjusted under 35 U.S.C. 154(b) by 0 days.

(21) Appl. No.: 16/664,082

(22) Filed: Dec. 5, 2019

(65) Prior Publication Data

US 2020/0221932 A1    Jul. 16, 2020

Related U.S. Application Data

(60) Provisional application No. 62/901,393, filed on Sep. 17, 2019, provisional application No. 62/897,352, filed on Sep. 8, 2019, provisional application No. 62/884,688, filed on Aug. 9, 2019, provisional application No. 62/880,677, filed on Jul. 31, 2019, provisional application No. 62/878,384, filed on Jul.

(Continued)

(51) Int. Cl.
| | |
|---|---|
| *A61B 1/00* | (2006.01) |
| *A61B 1/018* | (2006.01) |
| *A61B 1/06* | (2006.01) |
| *A61B 1/12* | (2006.01) |
| *A61L 2/07* | (2006.01) |
| *A61B 1/05* | (2006.01) |

(52) U.S. Cl.
CPC ...... *A61B 1/00105* (2013.01); *A61B 1/00016* (2013.01); *A61B 1/00034* (2013.01); *A61B 1/00052* (2013.01); *A61B 1/00103* (2013.01); *A61B 1/00124* (2013.01); *A61B 1/018* (2013.01); *A61B 1/05* (2013.01); *A61B 1/06* (2013.01); *A61B 1/121* (2013.01); *A61L 2/07* (2013.01); *A61L 2202/24* (2013.01)

(58) Field of Classification Search
CPC ... A61B 1/00103; A61B 1/00105; A61B 1/05; A61B 1/015; A61B 1/018; A61B 1/00066; A61B 1/00048; A61B 1/00034
See application file for complete search history.

(56) References Cited

U.S. PATENT DOCUMENTS

| | | | |
|---|---|---|---|
| 2009/0286412 A1* | 11/2009 | Ikeda | A61B 1/00128 439/271 |
| 2017/0188795 A1* | 7/2017 | Ouyang | A61B 1/00048 |

(Continued)

*Primary Examiner* — Alexandra L Newton
(74) *Attorney, Agent, or Firm* — Wissing Miller LLP (57) ABSTRACT

A handheld endoscope has a disposable, single-use portion that includes a distal tip, cannula, housings, and a proximal port that is connected to a substantially straight working channel. The cannula is rotatable about the main longitudinal axis of the cannula. The endoscope also includes a re-usable portion that has a handle and display module. The single-use and re-usable portions mate and un-mate with each other via physical side-mounting arrangement as well as separate electrical connectors. The handle can house imaging system electronics that support manual and auto imaging modes which can be selected via touch screen control on the display module. The re-useable portion is sealed with various o-rings and/or gaskets and can be highly fluid resistant to facilitate disinfecting and/or sterilization.

14 Claims, 11 Drawing Sheets

Related U.S. Application Data 25, 2019, provisional application No. 62/873,861, filed on Jul. 13, 2019, provisional application No. 62/870,748, filed on Jul. 4, 2019, provisional application No. 62/842,297, filed on May 2, 2019, provisional application No. 62/825,948, filed on Mar. 29, 2019, provisional application No. 62/821,536, filed on Mar. 21, 2019, provisional application No. 62/821,430, filed on Mar. 20, 2019, provisional application No. 62/797,235, filed on Jan. 26, 2019, provisional application No. 62/796,346, filed on Jan. 24, 2019, provisional application No. 62/795,042, filed on Jan. 22, 2019, provisional application No. 62/791,045, filed on Jan. 11, 2019.

(56) References Cited

U.S. PATENT DOCUMENTS

| | | | |
|---|---|---|---|
| 2019/0029497 A1* | 1/2019 | Mirza | A61B 1/00016 |
| 2019/0282073 A1* | 9/2019 | Truckai | A61B 1/015 |
| 2019/0320879 A1* | 10/2019 | Langell | A61B 1/00188 |
| 2019/0374095 A1* | 12/2019 | Lord | A61B 1/00066 |

\* cited by examiner

FIG. 11B

PORTABLE ENDOSCOPE WITH SIDE-MOUNTABLE DISPOSABLE PORTION

REFERENCE TO RELATED APPLICATIONS

This patent application claims the benefit of and incorporates by reference each of the following provisional applications:

U.S. Prov. Ser. No. 62/901,393 filed Sep. 17, 2019;
U.S. Prov. Ser. No. 62/897,352 filed Sep. 8, 2019
U.S. Prov. Ser. No. 62/884,688 filed Aug. 9, 2019
U.S. Prov. Ser. No. 62/880,677 filed Jul. 31, 2019
U.S. Prov. Ser. No. 62/873,861 filed Jul. 13, 2019
U.S. Prov. Ser. No. 62/870,748 filed Jul. 4, 2019
U.S. Prov. Ser. No. 62/878,384 filed Jul. 25, 2019
U.S. Prov. Ser. No. 62/842,297 filed May 2, 2019;
U.S. Prov. Ser. No. 62/825,948 filed Mar. 29, 2019;
U.S. Prov. Ser. No. 62/821,536 filed Mar. 21, 2019;
U.S. Prov. Ser. No. 62/821,430 filed Mar. 20, 2019;
U.S. Prov. Ser. No. 62/797,235 filed Jan. 26, 2019;
U.S. Prov. Ser. No. 62/796,346 filed Jan. 24, 2019;
U.S. Prov. Ser. No. 62/795,042 filed Jan. 22, 2019; and
U.S. Prov. Ser. No. 62/791,045 filed Jan. 11, 2019.

This patent application incorporates by reference each of the following provisional and non-provisional patent applications and issued patent(s):

U.S. Pat. No. 9,895,048 issued Feb. 20, 2018;
U.S. Pat. No. 9,895,858 issued Feb. 20, 2018;
U.S. Pat. No. 10,278,563 issued May 7, 2019;
U.S. Pat. No. 10,292,571 issued May 21, 2019;
U.S. Ser. No. 15/856,077 filed Dec. 28, 2017;
U.S. Ser. No. 16/407,028 filed May 8, 2019;
U.S. Ser. No. 16/413,160 filed May 15, 2019;
U.S. Ser. No. 15/462,331 filed Mar. 17, 2017;
U.S. Ser. No. 14/913,867 filed Feb. 23, 2016;
Intl Pat. App. No. PCT/US18/14880 filed Jan. 23, 2018;
Intl Pat. App. No. PCT/US16/65396 filed Dec. 7, 2016;
Intl Pat. App. No. PCT/US16/18670 filed Feb. 19, 2016;
U.S. Prov. Ser. No. 62/647,454 filed Mar. 23, 2018;
U.S. Prov. Ser. No. 62/634,854 filed Feb. 24, 2018;
U.S. Prov. Ser. No. 62/587,038 filed Nov. 16, 2017;
U.S. Prov. Ser. No. 62/551,264 filed Aug. 29, 2017;
U.S. Prov. Ser. No. 62/452,883 filed Jan. 31, 2017;
U.S. Prov. Ser. No. 62/449,257 filed Jan. 23, 2017;
U.S. Prov. Ser. No. 62/443,769 filed Jan. 8, 2017;
U.S. Prov. Ser. No. 62/416,403 filed Nov. 2, 2016;
U.S. Prov. Ser. No. 62/405,930 filed Oct. 9, 2016;
U.S. Prov. Ser. No. 62/375,814 filed Aug. 16, 2016;
U.S. Prov. Ser. No. 62/362,643 filed Jul. 15, 2016;
U.S. Prov. Ser. No. 62/339,810 filed May 21, 2016;
U.S. Prov. Ser. No. 62/299,453 filed Feb. 24, 2016
U.S. Prov. Ser. No. 62/287,901 filed Jan. 28, 2016;
U.S. Prov. Ser. No. 62/279,784 filed Jan. 17, 2016;
U.S. Prov. Ser. No. 62/275,241 filed Jan. 6, 2016;
U.S. Prov. Ser. No. 62/275,222 filed Jan. 5, 2016;
U.S. Prov. Ser. No. 62/259,991 filed Nov. 25, 2015;
U.S. Prov. Ser. No. 62/254,718 filed Nov. 13, 2015;
U.S. Prov. Ser. No. 62/139,754 filed Mar. 29, 2015;
U.S. Prov. Ser. No. 62/120,316 filed Feb. 24, 2015; and
U.S. Prov. Ser. No. 62/119,521 filed Feb. 23, 2015.

FIELD

This patent specification generally relates to a medical device for use in tissue examinations and endoscopic surgery such as in urology and gynecology. More particularly, some embodiments relate to a portable, handheld, low-cost surgical endoscope device having a single-use portion and a multiple-use portion.

BACKGROUND

Conventional endoscopy, or direct vision used to examine the interior of a hollow organ or cavity of the body, uses a complex lens system for transmitting the image from the distal tip of the endoscope to a viewer. The lens system is typically a relay lens system in the case of rigid endoscopes or a bundle of fiber optics or an objective lens system in the case of flexible endoscopes. In the case of both rigid and flexible conventional endoscopes, the lens or fiber optic system is relatively expensive and is intended to be re-used many times. Therefore, stringent decontamination and disinfection procedures need to be carried out after each use.

Disposable endoscopy is an emerging category of endoscopic instruments. In some cases the manufacture of endoscopes can be made inexpensive enough to be used on a single patient only. Disposable or single-use endoscopy lessens the risk of cross-contamination and hospital acquired diseases. Partially disposable endoscopy systems are discussed in U.S. Pat. Nos. 9,895,048, 9,895,848,10,278,563, and 10,292,571.

The subject matter described or claimed in this patent specification is not limited to embodiments that solve any specific disadvantages or that operate only in environments such as those described above. Rather, the above background is only provided to illustrate one exemplary technology area where some embodiments described herein may be practiced.

SUMMARY

According to some embodiments, an endoscope comprises: (a) a reusable handle that includes: an elongated side slot in a side of said reusable handle, extending in a direction along a longitudinal axis of the endoscope, a display module with a screen to display images, wherein said display module is mechanically mounted to said reusable handle for rotation and/or pivoting relative to the handle, signal processing circuits inside the reusable handle, operatively coupled with said display module, and a first electrical connector at said handle, operatively coupled to said signal processing circuits; (b) a single-use, disposable portion that includes: an insert housing configured to releasably snap into and release from said elongated side slot by motion relative to said handle in a direction transverse to said longitudinal axis, a cannula extending distally from the insert housing, wherein said cannula is configured for rotation about said longitudinal axis relative to said housing, a first lumen extending along said longitudinal axis, from a first proximal port that starts at a location proximal from both the insert housing and said handle and ends at a distal portion of the cannula, an imaging and illumination module at a distal portion of the cannula, a second electrical connector operatively coupled with said imaging and illumination module and configured to releasably mate with said first electrical connector to establish an electrical connection between said imaging and illumination module and said signal processing circuit; and (c) control buttons on at least one of the handle and the display module, coupled with said display module, signal processing circuits and imaging and illumination module to selectively cause the imaging and illumination module to illuminate a field of view and take images thereof and cause the display module to display said images.

According to some embodiments: the side slot in the reusable handle can extend from a proximal end of the handle to a distal end of the handle; the housing, when snapped into the side slot of the handle, can extent from the proximal end of the handle to the distal end of the handle; the handle can include an outside wall of plural components sufficiently sealed against each other to enable repeated steam-sterilizing of said handle; the endoscope can include a removable plug closing off the first electrical connector to assist in sealing the handle for repeated steam-sterilizing; o-rings and/or gaskets can be used to seal the components of the handle against each other; the first electrical connector can be configured for coupling to external equipment such as one or more of a workstation and image archiving and/or transmitting units for sending thereto images taken with said imaging and illumination module; the endoscope can include a cable electrically coupling the second electrical connector with the imaging and illumination module, wherein said cable has a distal portion inside the cannula and a proximal portion that is outside the cannula and the housing and is sufficiently long and flexible to enable rotation of the cannula relative to the handle about said longitudinal axis of at least 180 degrees when the housing is snapped in said side slot of the handle and the first and second connectors are mated; the endoscope can include a second proximal port extending proximally from the proximal ends of both the housing and the handle when the housing is snapped into the handle side slot; the endoscope can include an intermediate port that is distal from the handle when said housing is snapped into the handle but is proximal from the distal portion of the cannula; the endoscope can include a second lumen extending along the longitudinal axis and fluidly coupled with at least one port that is in addition to the first proximal port; the first port can be vertically in line with a center of the display module and less than 15 cm from the center of the display module, thereby placing the first port in a line and angle of site of a viewer that includes both the display module and the first port; the handle can include a rechargeable battery, and the first electrical connector can be coupled electrically with the battery to enable charging the battery through the first electrical connector; and the signal processing circuits in the handle can include WiFi circuits and the endoscope can include an antenna configured to wirelessly transmit images taken with the imaging and illumination module.

In some embodiments, a single-use, disposable portion of an endoscope comprises: an insert housing elongated along a longitudinal axis; a cannula extending distally from the insert housing; wherein the housing is configured to releasably snap into and release from an elongated side slot of a reusable handle by motion relative to said handle in a direction transverse to the longitudinal axis; wherein the cannula is configured to rotate about the longitudinal axis relative to said housing; a first lumen extending along the longitudinal axis, from a first proximal port that starts at a location proximal from the insert housing and ends at a distal portion of the cannula; an imaging and illumination module at a distal portion of the cannula; an electrical connector operatively coupled with said imaging and illumination module; and a cable electrically coupling the imaging and illumination module with said electrical connector; wherein the cable has a distal portion inside said cannula and a proximal portion that is outside the cannula and the housing and is sufficiently long and flexible to enable rotation of at least 180 degrees of the cannula relative to the housing about the longitudinal axis.

In some embodiments, an endoscopic apparatus comprises: a reusable handle with a pistol grip configured for grasping with a user's hand; an elongated side slot in a side of the reusable handle, above the pistol grip and extending along a longitudinal axis of the handle that is transverse to a direction in which the pistol grip extends; wherein the side slot is configured for removably snap-fitting a housing therein from which a cannula with an imaging module at a distal end thereof extends distally; a display module with a screen to display images, mounted to an upper portion of the handle for rotation and/or pivoting relative to the handle; image processing circuits inside the handle, operatively coupled with the display module and configured to display images sent thereto from the imaging module; and an electrical connector at said handle, operatively coupled to the image processing circuits and configured to receive images taken with the imaging module at a distal end of a cannula.

In some embodiments, a method of imaging an internal site in a patient comprises: providing a cannula extending distally from a housing that is elongated along a longitudinal axis of the cannula, said cannula and housing forming a single-use, disposable portion of an endoscope; providing, as a reusable portion of the endoscope, a handle that has a side slot elongated in the direction of said longitudinal axis and extending from a proximal end to a distal end of the handle, and a display module secured to the handle to rotate and/or pivot relative to the handle; snap-fitting the housing in the side slot of the handle such that the housing extends from the proximal to the distal end of the handle; electrically coupling an imaging module at a distal end of the cannula to electronic circuits in the handle that are electronically coupled to said display module; wherein the coupling comprises providing a cable between the imaging module and a first connector, providing a second connector at the housing, and mating said connectors; wherein providing the cable comprises providing a cable that has a distal portion running inside the cannula and a proximal portion that is outside the cannula and the housing and is exposed to the environment; transmitting, over the cable and connectors and the electronic circuits, images taken with said imaging module to said display unit for display to users; and selectively rotating the cannula relative to the housing and handle to image selected areas and display selected images.

In some embodiments, the method additionally includes: making the exposed part of the cable sufficiently long to enable rotation of the cannula relative to the housing and the handle of at least 180 degrees; repeatedly sterilizing the handle in steam; providing the handle with an exterior wall of plural portions and sealing them against each other using o-rings and/or gaskets to enable sterilizing the handle in steam and providing a fluid port at a location proximal to both the handle and the housing and a lumen that extends along the longitudinal axis from the port to a distal portion of said cannula.

As used herein, the grammatical conjunctions "and", "or" and "and/or" are all intended to indicate that one or more of the cases, object or subjects they connect may occur or be present. In this way, as used herein the term "or" in all cases indicates an "inclusive or" meaning rather than an "exclusive or" meaning.

As used herein the terms "surgical" or "surgery" refer to any physical intervention on a patient's tissues, and does not necessarily involve cutting a patient's tissues or closure of a previously sustained wound.

BRIEF DESCRIPTION OF THE DRAWINGS

To further clarify the above and other advantages and features of the subject matter of this patent specification, specific examples of embodiments thereof are illustrated in the appended drawings. It should be appreciated that these drawings depict only illustrative embodiments and are therefore not to be considered limiting of the scope of this patent specification or the appended claims. The subject matter hereof will be described and explained with additional specificity and detail through the use of the accompanying drawings in which:

DETAILED DESCRIPTION

A detailed description of examples of preferred embodiments is provided below. While several embodiments are described, it should be understood that the new subject matter described in this patent specification is not limited to any one embodiment or combination of embodiments described herein, but instead encompasses numerous alternatives, modifications, and equivalents. In addition, while numerous specific details are set forth in the following description in order to provide a thorough understanding, some embodiments can be practiced without some or all of these details. Moreover, for the purpose of clarity, certain technical material that is known in the related art has not been described in detail in order to avoid unnecessarily obscuring the new subject matter described herein. It should be clear that individual features of one or several of the specific embodiments described herein can be used in combination with features of other described embodiments or with other features. Further, like reference numbers and designations in the various drawings indicate like elements. All patents and patent applications identified in this detailed description are hereby incorporated by reference in this patent specification.

Figures 1, 2:
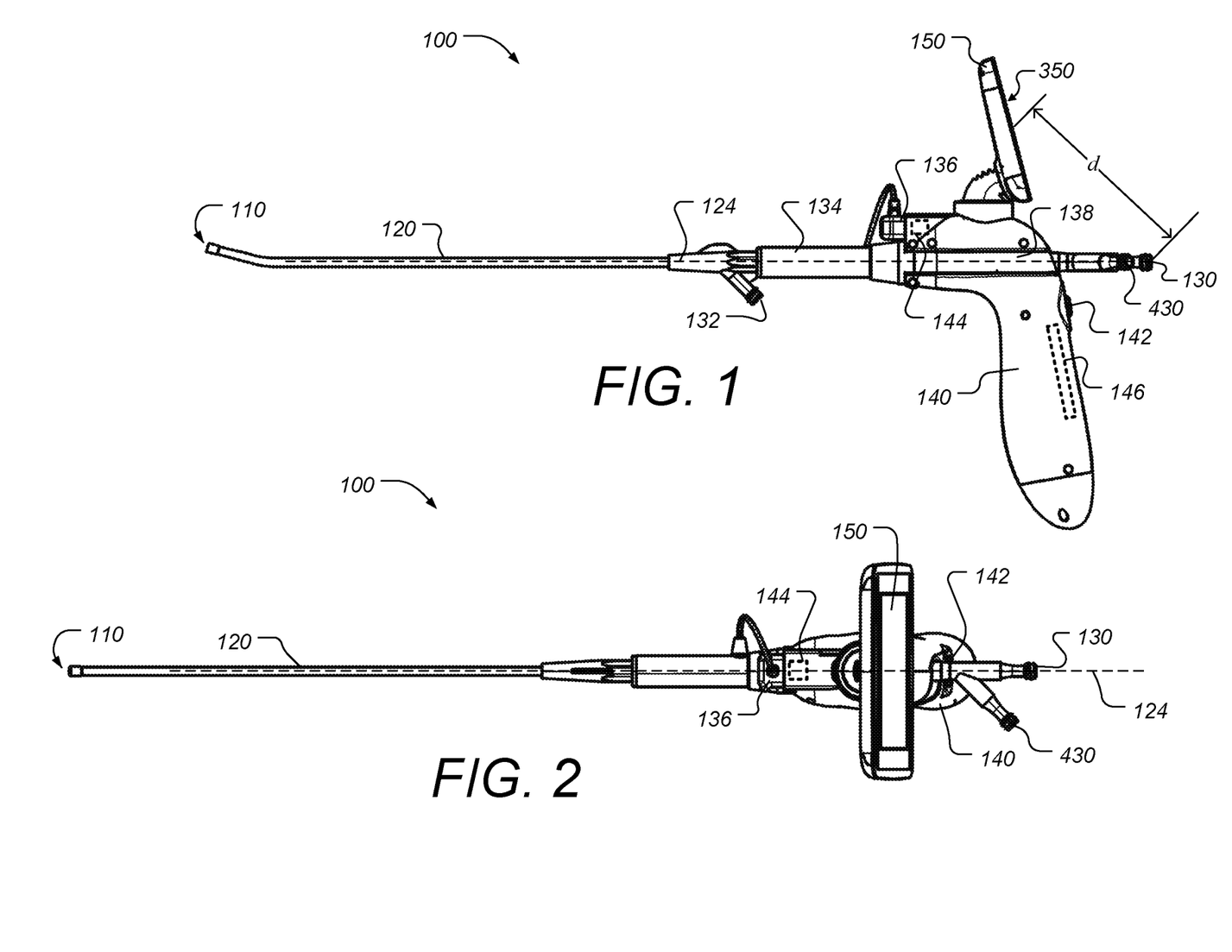
FIGS. 1 and 2 are right side and top views, respectively, of a portable endoscope having a disposable side-mountable portion, according to some embodiments.

FIGS. 1 and 2 are right side and top views, respectively, of a portable endoscope having a disposable portion, according to some embodiments. The portable endoscope 100 includes an elongated cannula 120 with a distal tip 110 for inserting into a hollow organ or cavity of the body. According to some embodiments, distal tip 110 is formed as a separate distal tip sub-assembly that is attached to the cannula 120. According to some embodiments, the distal tip 110 is about than 4.55 mm in diameter. For further details relating to a separate tip sub-assembly for a handheld endoscope, see: U.S. Pat. No. 9,895,048 (hereinafter referred to as "the '048 patent"); U.S. Ser. No. 15/462,331 filed Mar. 17, 2017 published as U.S. 2017-0188793 A1 (hereinafter the '331 application); and Intl Pat. App. No. PCT/US18/14880 filed Jan. 23, 2018 published as Intl Pub. No. WO/2018/136950 (hereinafter referred to as "the '880 application"). Distal tip 110 includes an imaging module and one or more LED light sources for viewing the organ or cavity into which tip 110 is inserted. The tip 110 also includes one or more fluid ports.

According to some embodiments, the cannula 120 is rigid, flexible or semi flexible and includes one or more fluid channels which are fluidly connected to port 132. Port 132 includes a Luer fitting to facilitate leak-free connection of port 132 with various medical fluid components (not shown). The one or more fluid channels or lumens in cannula 120 are also connected to one or more distal facing fluid ports of distal tip 110. According to some embodiments, one or more of the fluid channels or lumens in cannula 120 are also connected to proximal ports 130 and 430. Proximal ports 130 and 430 also include Luer fittings to facilitate leak-free connection with various medial fluid components (not shown). According to some embodiments, proximal port 130 is substantially in-line with the main longitudinal axis 124 of cannula 120 and thereby provides a substantially straight working channel through which rigid or semi rigid tools can pass through. According to some embodiments, only one proximal port 130 is provided and the second proximal port 430 is omitted. Providing a device channel that has straight proximal portion (through port 130), allows for improved ease in device insertion and manipulation. It has been found that providing the device port(s) (e.g. ports 130 and/or 430) in close proximity to the display module 150, and vertically in line with a center of display 150, provides significant ergonomic benefits. This placement makes it easier to insert a surgical instrument in port 130 or 430 and easier to manipulate the instrument because, to the user's eyes, the instrument is within the same sight and angle of the display screen. In particular, a short distance between the ports and display screen allows the operator to confine his/her range of vision to a relatively small area. According to some embodiments, the distance d between the proximal port (in this case port 130) and the center of the screen 350 of display module 150 is less than about 15 cm. According to some embodiments, the distance d is less than about 12 cm. According to some embodiments, the distance d is less than about 10 cm.

According to some embodiments, all three ports 130, 132 and 430 are connected to the same lumen or channel within cannula 120 and according to other embodiments, the ports are connected to two or more separate lumens. In the case where two or more ports are connected to a single lumen in cannula 120, one or more "duck bill" or similar valves can be used to prevent back flow or leak. According to some embodiments, wires running from the LED light sources and camera module in tip assembly 110 pass through a separate channel in cannula 120 to electrical connector 136 that is in addition to the one or more fluid channels. Electrical connector 136 is configured to form a releasable electrical connection with handle electrical connector 144 on the handle portion 140. Proximal to the fluid port 132 are a housing 134 and insert housing 138. According to some embodiments, the insert housing 138 is configured to slidably mate with, e.g., snap-fit in, a side-slot formed in handle 140 (see side-slot or socket 440 in FIG. 4A).

The endoscope 100 includes a handle portion 140 that is sized and shaped in a pistol-like fashion for easy grasping in a pistol-like grip by the endoscope operator (e.g. doctor or other medical professional). A display module 150 is rotatably and/or pivotally mounted on handle 140 via a bearing which can be a plain bearing made of plastic, and a rubber coated hinge. Also visible on handle 140 is image capture button 142. According to some embodiments handle 140 and display module 150 are configured to be re-usable and make up reusable portion 402 (shown in FIGS. 4A and 4B). According to some embodiments, one or more electronics modules 146 are included in handle 140, including electronics configured to provide one more of the following: camera control, video capture, video processing, video/data storage, battery charging and control, touch-screen processing, and WiFi communication. According to some embodiments, the electronics modules 146 include an electronic imaging system that supports automated features such as exposure control (AEC), gain control (AGO) and white balance (AWB). In addition, the electronics modules 146 are configured to provide ALC (auto light control) which controls the illumination of the object to be imaged. The camera and illumination modules in distal tip 110 and the imaging and control in electronics modules 146 are together configured as a "well-tuned" imaging system that provides a useful "Auto Mode." According to some embodiments, handle 140 is similar to handle 140 shown and described in the '048 patent, the '331 application, and the '880 application in that all are generally pistol-grip handles and may contain electronics and are coupled with displays, but handle 140 in the subject application differs in significant ways, including in the way it releasable couples and interacts with disposable portion 400.

Figure 3:
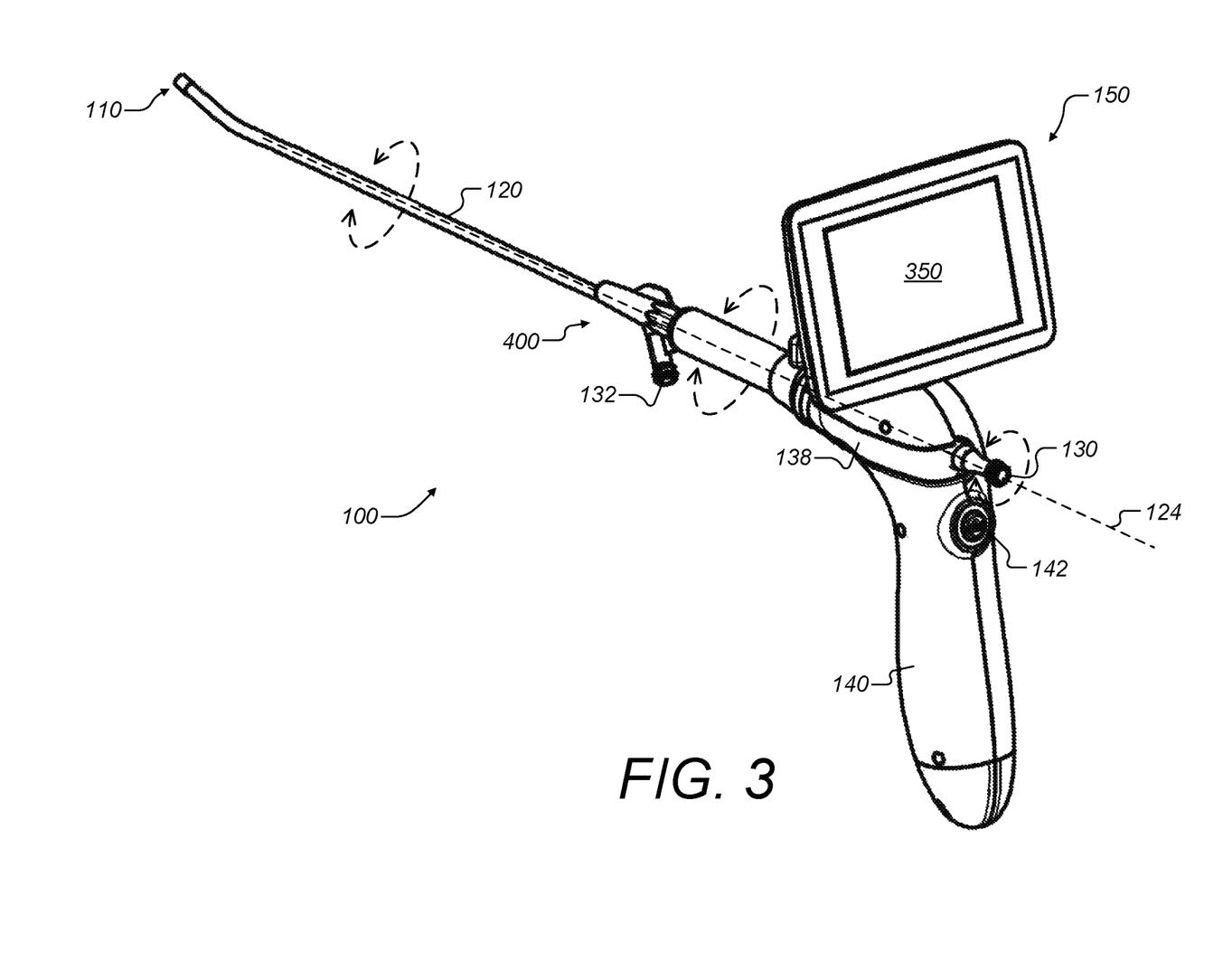
FIG. 3 is a perspective view of a portable endoscope having a disposable side-mountable portion, according to some embodiments.

FIG. 3 is a perspective view of a portable endoscope having a disposable side-mountable portion, according to some embodiments. The version of endoscope 100 shown includes only a single proximal port 130. According to some embodiments, different versions of the disposable single-use portion 400 can be made available to users depending upon their particular needs. Some examples are disposable portions in which an injection needle can protrude from the cannula tip, in a manner similar to that described in U.S. Pat. No. 10,278,563, or disposable portions with cannulas that have bendable distal ends, for example as described in U.S. patent application Ser. No. 16/447,251 filed Jun. 20, 2019, or disposable portions with cannulas that include a working channel through which surgical tools can pass, for example as in US 2019/0282071 A1, or disposable portions with cannulas that have distal ends shaped to scrape or otherwise take samples of tissue, for example as in U.S. Pat. No. 8,460,182. As shown by the dashed arrows, according to some embodiments the cannula 120 is rotatable about its longitudinal axis 124.

Figure 4A:
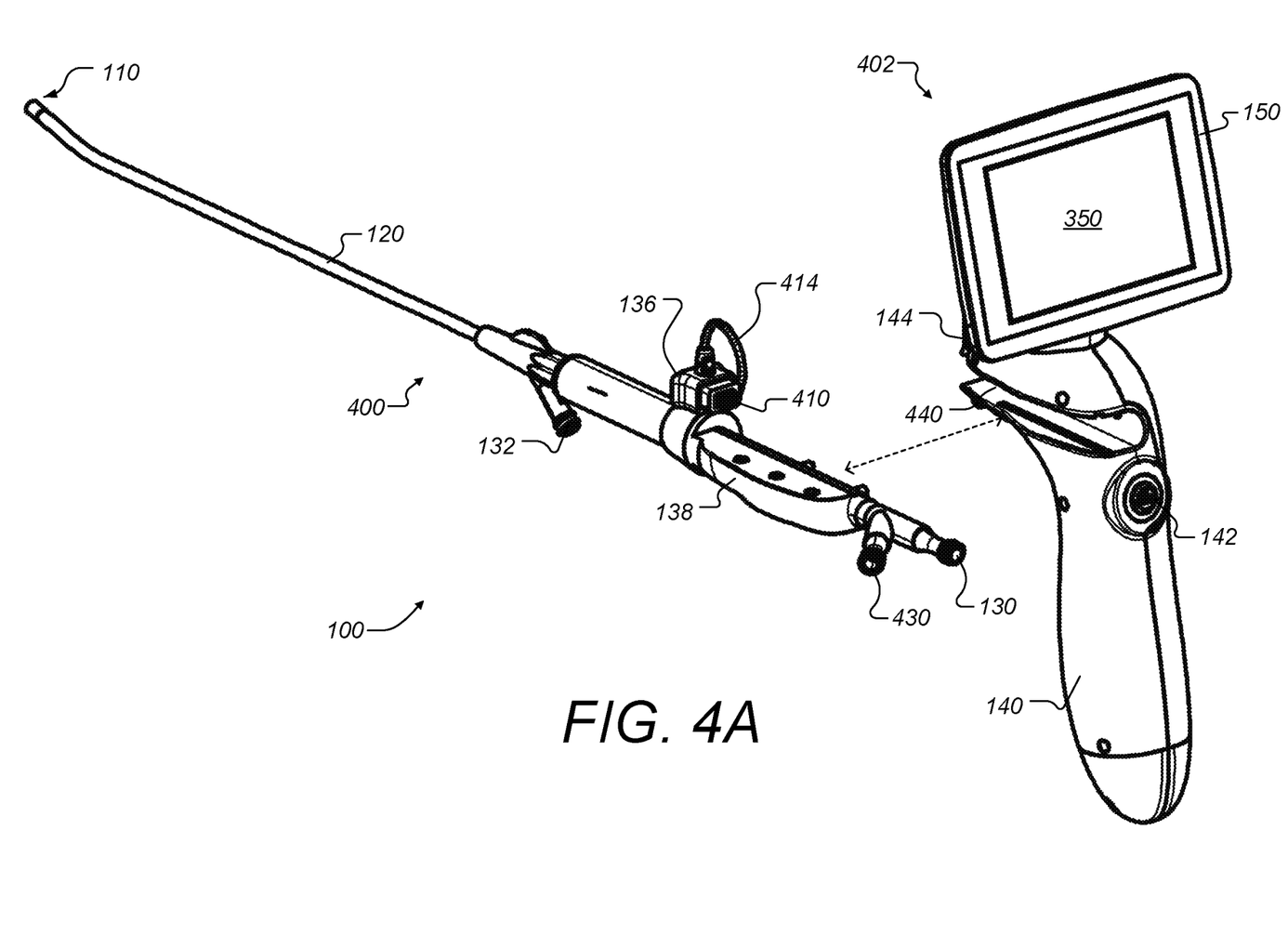
FIGS. 4A and 4B are perspective views illustrating further aspects of a portable endoscope having a side-mountable disposable portion, according to some embodiments.
Figure 4B:
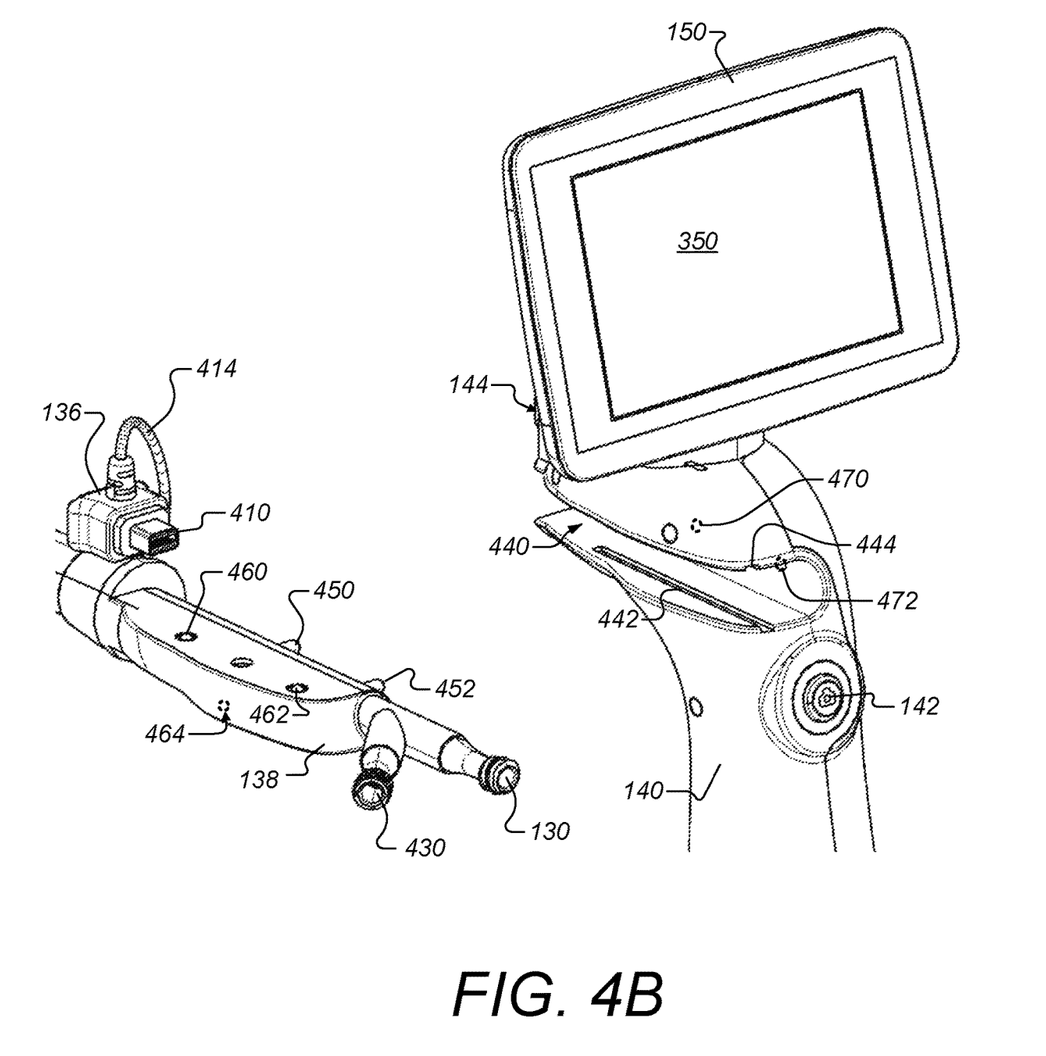

FIGS. 4A and 4B are perspective views illustrating further aspects of a portable endoscope having a side-mountable disposable portion, according to some embodiments. Illustrated more clearly in FIG. 4A are the single-use disposable portion 400 and the multi-use reusable portion 402 of endoscope 100. Single use portion 400 includes cannula 120, distal tip 110, electrical connector 136, ports 130, 132 and 430, and insert housing 138. The reusable portion 402 includes the handle 140 and display module 150. As shown by the dashed arrow, the single use portion 400 slides into the side of the reusable portion 402, by motion in a direction transverse to longitudinal axis 124. In particular, the insert housing 138 of single use portion 400 is dimensioned to fit snugly but releasably into the side slot 440 formed in handle 140 of reusable portion 402. The mating of insert housing 138 into slot 440 is configured to provide a secure physical connection between single use portion 400 and reusable portion 402. The electrical connections between the two portions 400 and 402 are made using electrical connector 136 and handle electrical connector 144. Separating the physical connections from electrical connections has been found to provide advantages such as greater resistance to fluid contamination to the electrical components and easier and more intuitive mating of the disposable and reusable portions. In addition, this type of electrical connection enables the alternative of conveniently connecting the disposable portion 400 to an electronic unit other than handle 140, such as a tower that contains computing equipment and a display or some other image processing and/or image storage equipment or equipment for transmitting images from portion 402 to remote locations such as hospital workstations or remote medicine facilities. According to some embodiments, the electrical connector 136 is connected to the body of single use portion 400 via a flexible cable 414, and is configured to allow for rotation of the cannula as shown in the dashed arrows of FIG. 3. A distal portion of cable 414 is inside cannula 120 but a proximal portion is outside, exposed to the environment, and is sufficiently long to enable rotation of cannula 120 relative to housing 134 and handle 140.

FIG. 4B shows further details of the physical and electrical connections between the single use portion and reusable portion of portable endoscope 100. According to some embodiments, the electrical connectors 136 and 144 use a standard electrical connection scheme such as mini-display port (type DP20), which is also used for versions 1 and 2 of Thunderbolt connectors. In FIG. 4B a male connector 410 is shown that can mate with a female connector 144 on handle 140. For the mechanical connection, the insert housing 138 can include positioning aids such as positioning balls 460, 462 and 464 which are spring-loaded and can engage with grooves 442 and 444 formed within slot 440. Additionally, posts 450 and 452 are formed on insert housing 138 and mate with holes 470 and 472 on the inside of slot 440 of handle 140.

Figure 5:
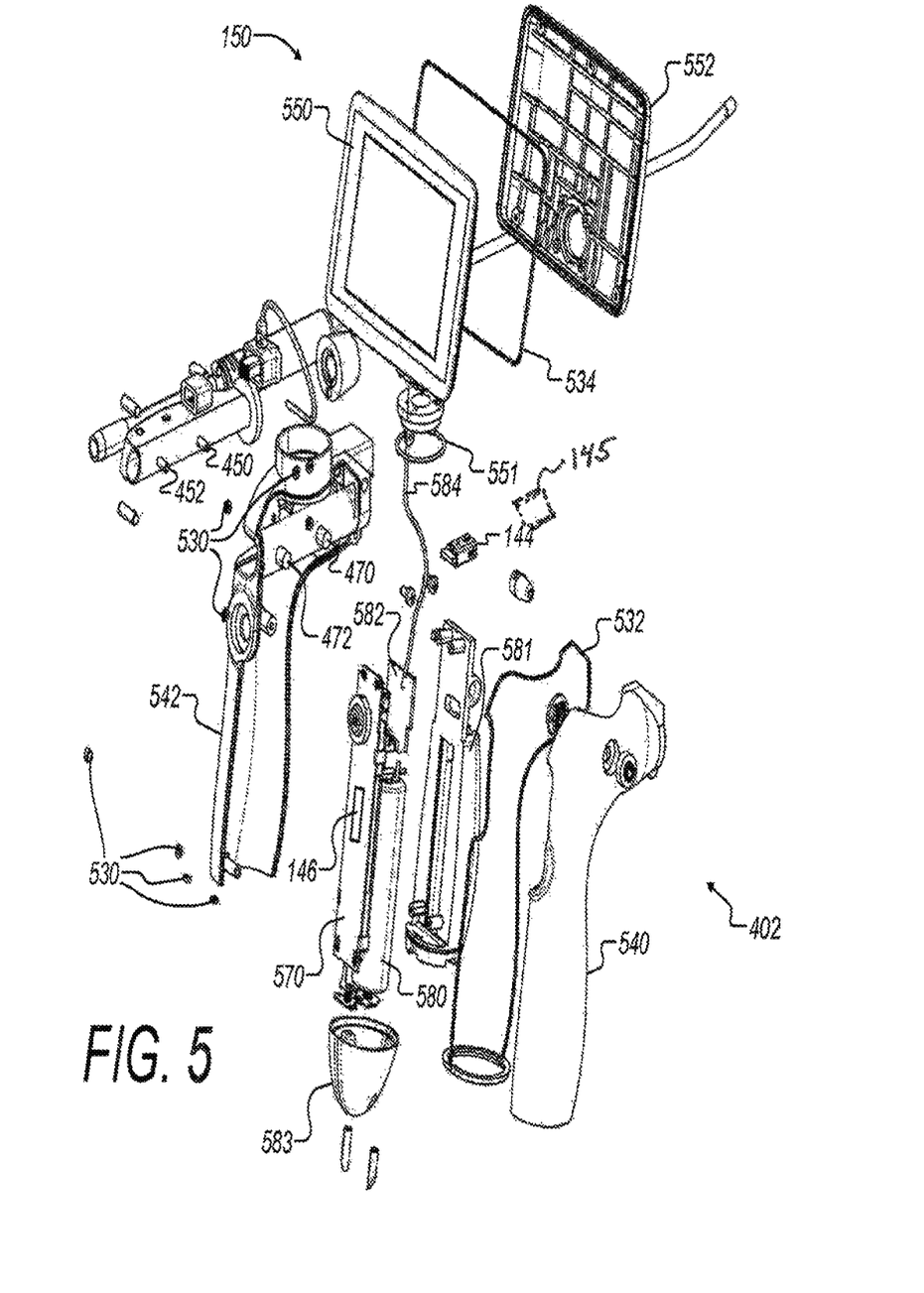
FIG. 5 is an exploded perspective illustrating sealing and other aspects of a portable endoscope having a side-mountable disposable portion and a fluid-resistant handle portion, according to some embodiments.

FIG. 5 is an exploded perspective view illustrating sealing and other aspects of a portable endoscope having a side-mountable disposable portion and a fluid-resistant handle portion, according to some embodiments. Many of the components of the reusable portion 402 are sealed using o-rings and/or gaskets, including left and right handle cover pieces 542 and 540, respectively, which are sealed to each other using an o-ring or gasket 532. Similarly, the front cover 550 and rear cover 552 of the display module 150 is sealed using an o-ring 534. The display module 150 are sealed to the left handle cover piece 542 using o-ring 551. Various other openings are sealed with o-rings such as o-rings 530. Front cover 581 and bottom cover or piece 583 similarly may be sealed against right and left handle cover pieces 540 and 542 by o-rings and/or gaskets.

Also shown in FIG. 5 is the main printed circuit board 570 on which electronics modules 146 are mounted. Rechargeable lithium ion battery 580 is used to power the electronics, display module 150, and also the camera module and LEDs on the distal tip through electrical connector 144. According to some embodiments, Wi-Fi functionality is included, and shown in FIG. 5 are WiFi board 582 and WiFi antenna 584.

Figure 6:
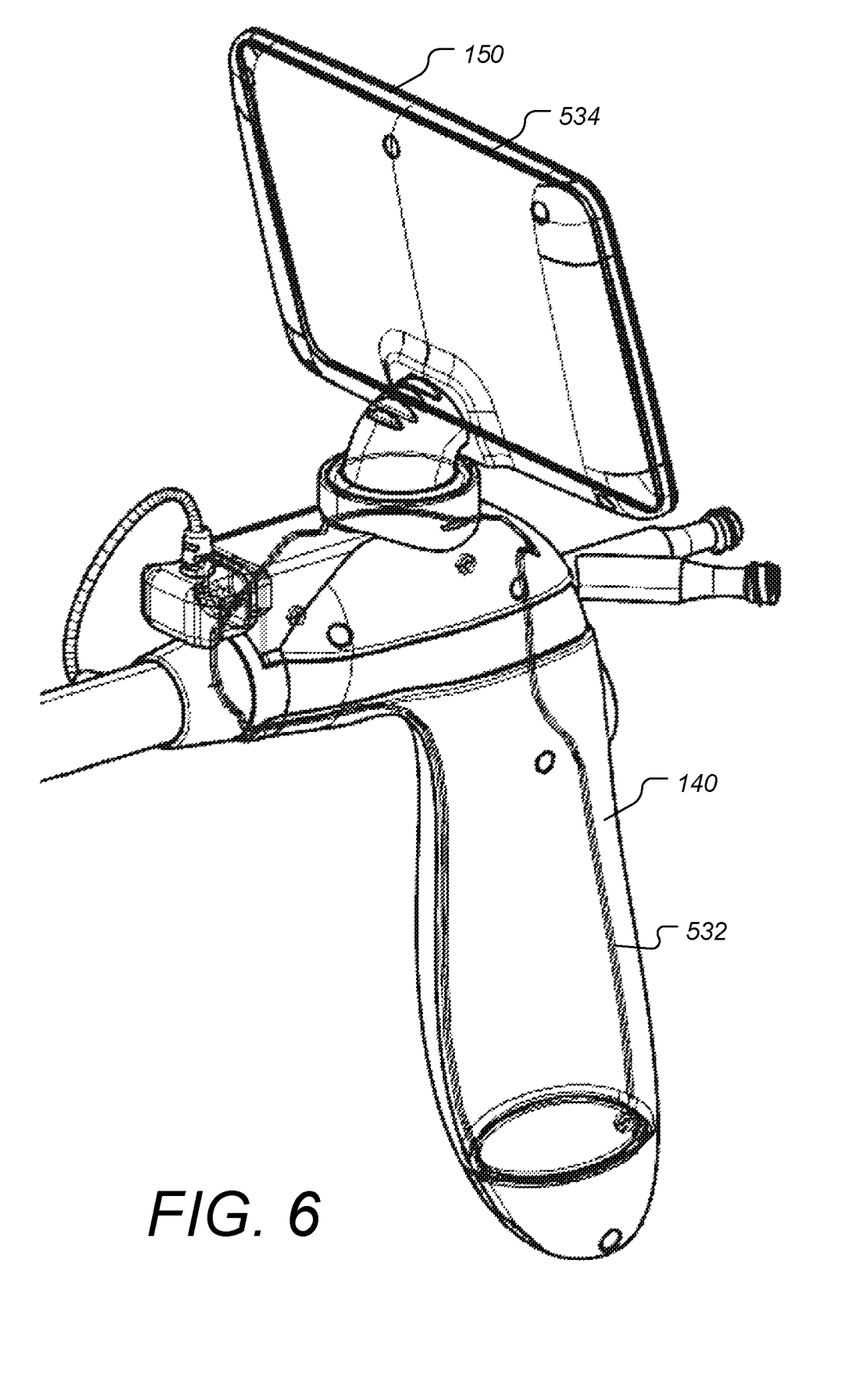
FIG. 6 is a perspective view illustrating sealing and other aspects of a portable endoscope having a side-mountable disposable portion, according to some embodiments.

FIG. 6 is a perspective view illustrating sealing and other aspects of a portable endoscope having a side-mountable disposable portion, according to some embodiments. The o-ring seals 532 and 534 are shown in this view. The o-ring seals shown and described in FIGS. 5 and 6 enable the reusable portion 402 of the portable endoscope to be highly water resistant. For example, handle 140 can be configured to comply with the IXP 7 standard and can withstand being submerged for up to 30 minutes 0.15 meters to 1 meter below a fluid surface. Following use, endoscope components that will be re-used can be disinfected and/or sterilized prior to re-use to prevent cross contamination. According to some embodiments, providing the sealing as shown and described provides a level of fluid-resistance for the reusable portion 402 to be soaked in fluid such as an alcohol, for cleaning, disinfection and/or sterilization. According to some embodiments, with the addition of a silicone plug 145 to seal the electrical connector 144, reusable portion 402 can be sterilized by submersion in EO (Ethylene oxide). According to some other embodiments, the reusable portion 402 is constructed such that it can withstand repeated autoclave such as hot steam at 134° C.

Figure 7:
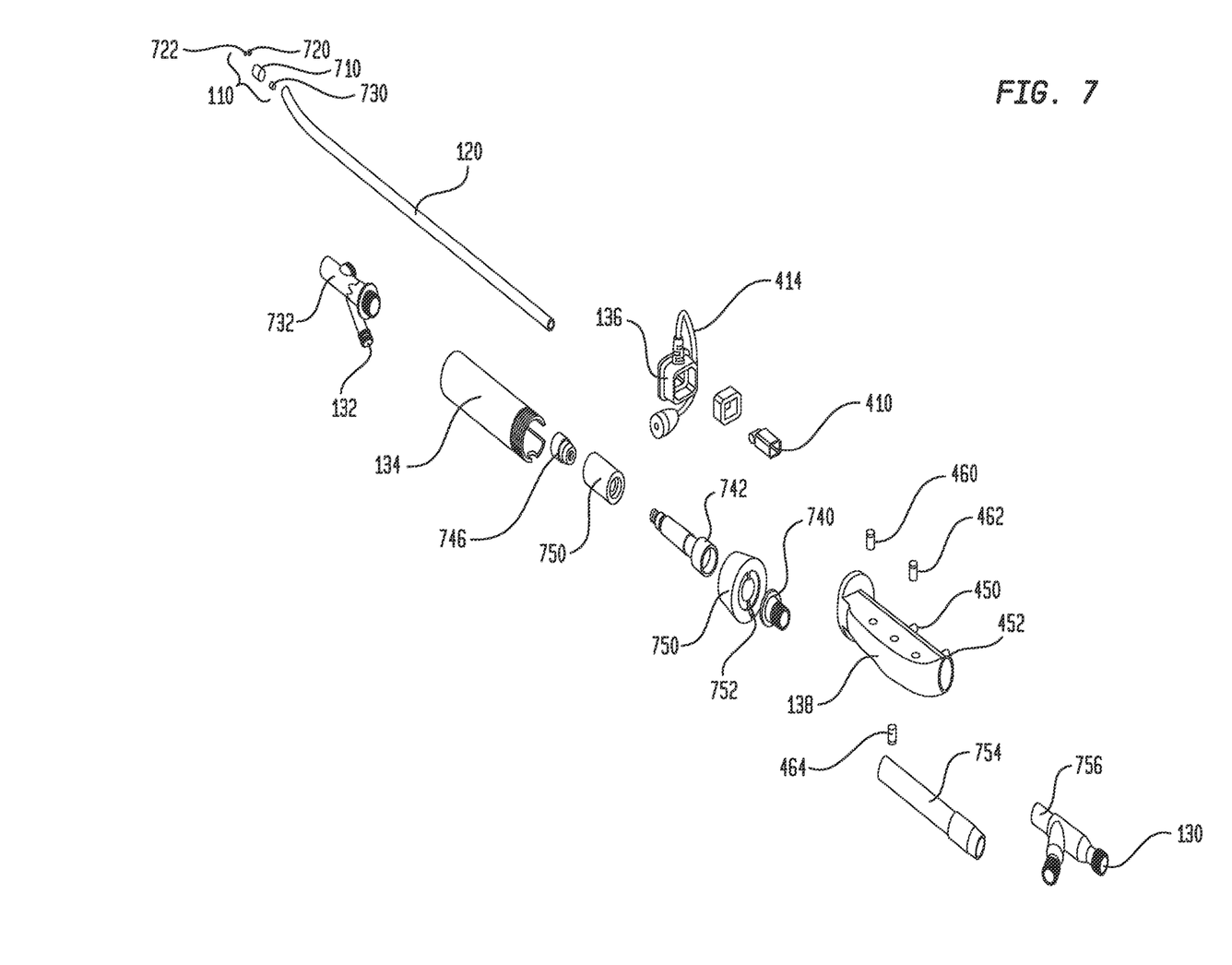
FIG. 7 is an exploded perspective illustrating cannula rotation and other aspects of a portable endoscope having a side-mountable disposable portion, according to some embodiments.

FIG. 7 is an exploded perspective illustrating cannula rotation and other aspects of a portable endoscope having a side-mountable disposable portion, according to some embodiments. At the distal end, distal tip 110 is shown to include tip housing 710, two or more LEDs of which only LEDs 720 and 722 are shown as an example, and camera module 730. The proximal end of cannula 120 is inserted into the distal end of fluid hub body 732. Hub body 732 is fixed at its proximal end to housing 134, which in turn is fixed at its proximal end to base 750. Within housing 134 is insert tube connector 746 that is shaped at its distal end to accept the proximal end of cannula 120. Connector 746 is connected at its proximal end to connector piece 744 which can be attached to connector 746 by screw threads and/or epoxy. The connector piece 744 is attached to joint-working channel piece 742. The base 750 is held in place by being "sandwiched" between flanges on the proximal end of channel piece 742 and on connector piece 740. Piece 740 is attached to tube 754. The proximal end of tube 754 is fixed to luer port piece 756. Tube 754 is configured to rotate freely within insert housing 138. The insert housing 138 and electrical connector 136 remain stationary relative to the handle 140, while most of the other components rotate about axis 124. In particular, according to some embodiments, the following components rotate together about axis 124 as a single unit: distal tip 110, canula 120, hub 732, housing 134 connectors 746 and 744, joint-working channel piece 742, base 750, connector piece 740, tube 744, and luer piece 756. According to some embodiments, the rotation of the cannula 120 and other components is limited to slightly less than 360 degrees (e.g. 350 degrees such as shown in FIG. 8B, or at least 180 degrees) so that flexible cable 414 does not become overly strained due to excessive rotation. The base 750 can include a tab 752 that fits into a circular slot 810 formed in on the distal face of the flange of insert housing 138 (shown in FIG. 8A)

Figure 8A:
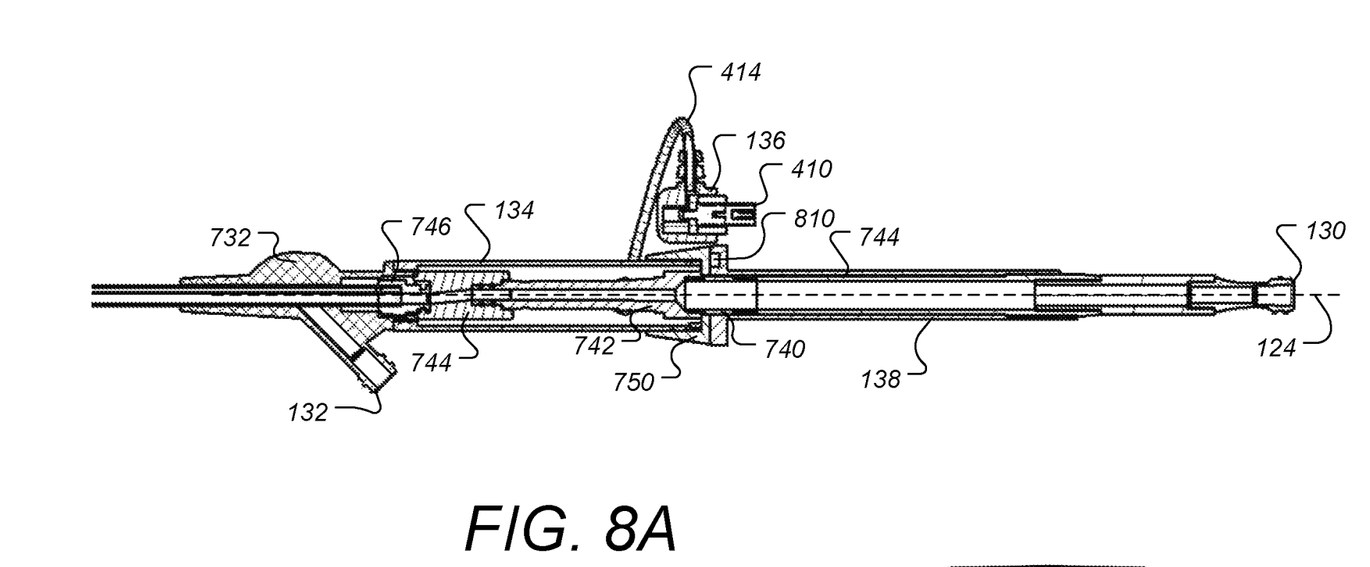
FIGS. 8A and 8B are cross section and frontal view illustrating cannula rotation and other aspects of a portable endoscope having a side-mountable disposable portion, according to some embodiments.
Figure 8B:
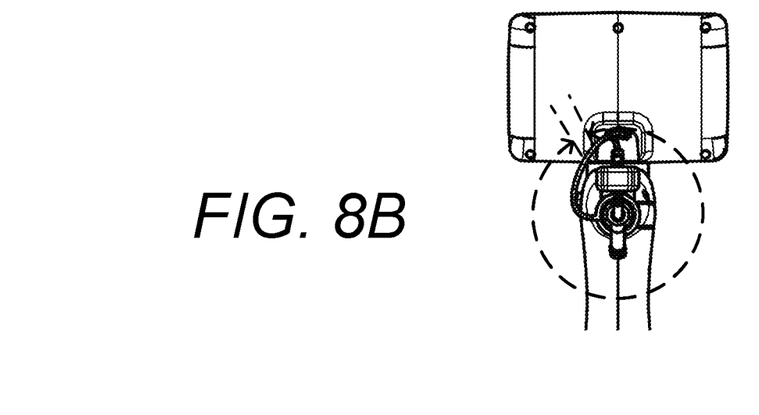

FIGS. 8A and 8B are cross section and frontal view illustrating cannula rotation and other aspects of a portable endoscope having a side-mountable disposable portion, according to some embodiments. According to some embodiments, slot 810 is shaped to limit the rotation of the cannula 120 and other components by limiting the movement of tab 752 (shown in FIG. 7) of base 750. Note that the working channel in the cannula may be slightly off center or off axis 124 due to the cannula containing multiple lumens. The connector piece 744 can be shaped to bring the working channel more towards the central longitudinal axis 124.

Figure 9:
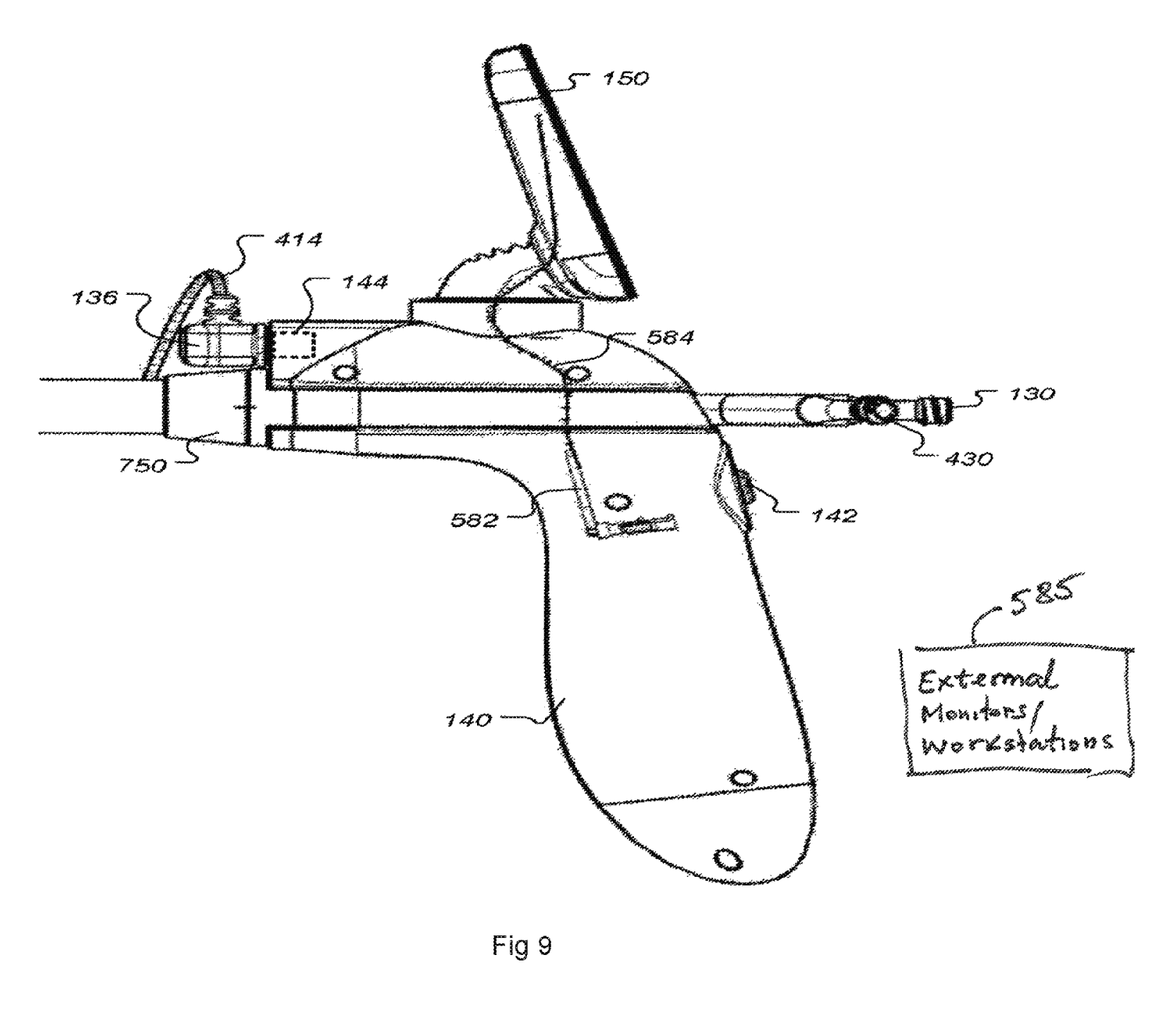
FIG. 9 is a side view illustrating a WiFi antenna arrangement and other aspects of a portable endoscope having a side-mountable disposable portion, according to some embodiments.

FIG. 9 is a side view illustrating a WiFi antenna arrangement and other aspects of a portable endoscope having a side-mountable disposable portion, according to some embodiments. WiFi board 582 and the location of WiFi antenna 584 is shown. Note that WiFi antenna 584 can extend to and along the back of the touch screen of display module 150 to reduce the effects of screening by metal portions of handle 140. According to some embodiments, the WiFi module on board 582 and the antenna 584 can transmit video to WiFi receivers which can be used for other external monitors or to workstations 585, for example.

Figure 10:
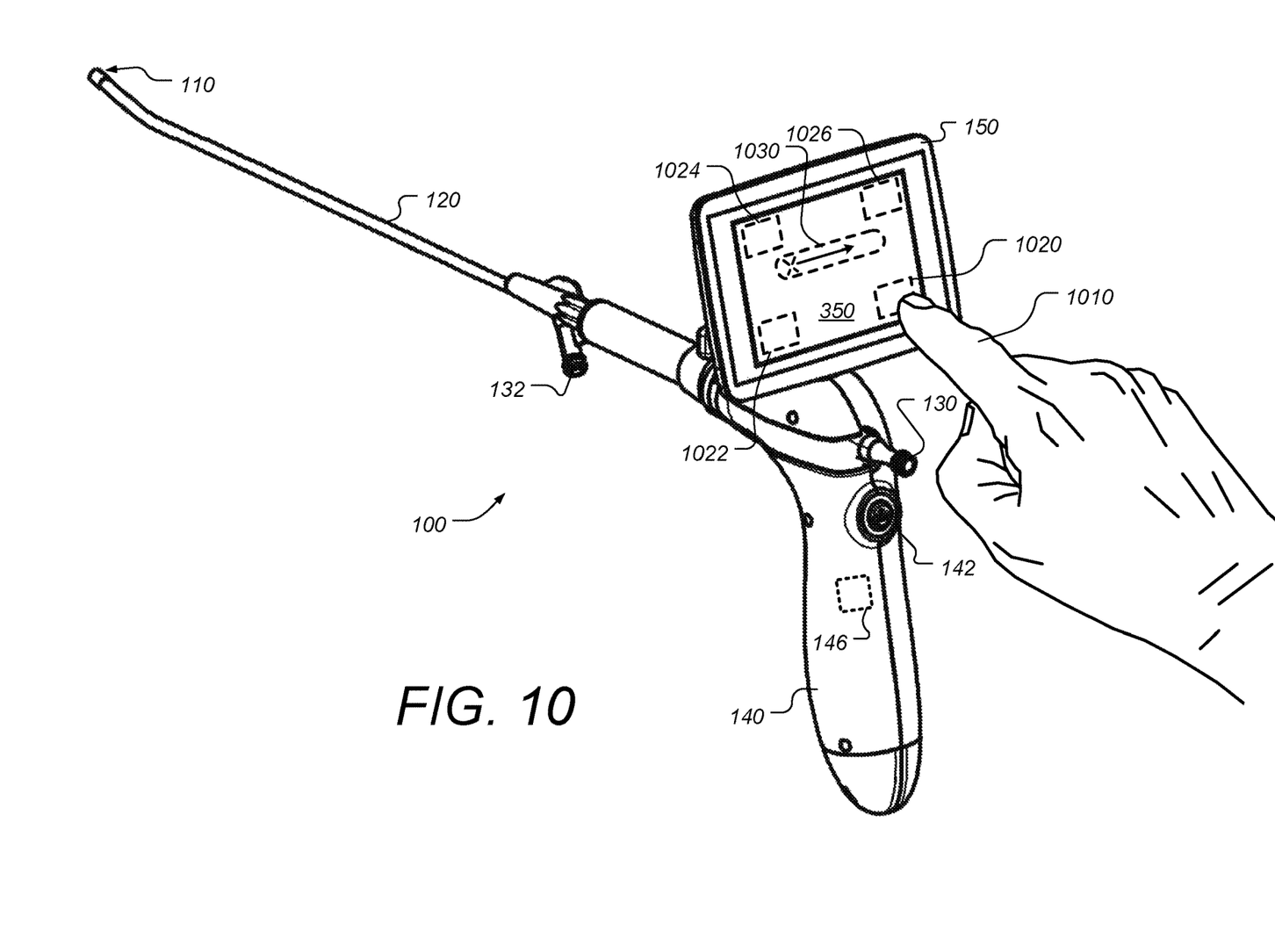
FIG. 10 is a perspective view illustrating aspects of a touch sensitive video display screen, according to some embodiments.

FIG. 10 is a perspective view illustrating aspects of a touch sensitive video display screen, according to some embodiments. As described supra, electronics modules 146 in handle 140 include an electronic imaging system that supports automated features such as exposure control (AEC), gain control (AGC) and white balance (AWB). In addition and integrated, is the ALC (auto light control) which controls the illumination of the object to be imaged. The camera and illumination modules in distal tip 110 and the imaging and control in electronics modules 146 are together configured as a "well-tuned" imaging system that provides a useful "Auto Mode." However, in certain cases, especially in endoscopy, it is sometimes advantageous to use a "Manual Mode". In a handheld portable endoscope 100, when the distal tip 110 is inside a cavity, Auto Mode works well in most situations. But in certain situations, for example when the camera on distal tip 110 is proximal to a wall that is tangential with the direction of the view of the camera module, part of the image field (the wall due to its proximity to the illuminating LEDs) is very bright compared to other areas which are further away from the LEDs. In order to better visualize the wall (or the portion that is close up to the camera tip), a "Manual Mode" can be used in which all the automated imaging functions are turned off. In FIG. 10, a toggle button such as one of the corner location buttons 1020, 1022, 1024 and 1026 on the touch screen 350 can be used to toggle or switch between Auto Mode and Manual Mode. According to some other embodiments, a hardware button on the handle 140 can be used instead of or in addition to the touch screen button, to switch between the Auto Mode and Manual Mode. Furthermore, the "Manual Mode" can have 2 or 3 steps to reduce the LED brightness to facilitate the visualization of the surface of interest. Some aspects of such Auto Mode and Manual Mode are described in U.S. Pat. No. 10,292,571.

According to some embodiments, Auto Mode is configured to provide full automatic AGC, AEC and ALC, while Manual Mode turns off AGC, AEC and ALC, and sets the LED brightness at 50% (or some other predetermined level such as 75%) of its default brightness Screen 350 can be configured for non-contact or non-touch operation such that clinical operators need not remove their gloves in order to push and activate a button on the screen 150. According to some embodiments, buttons 1020, 1022, 1024 and 1026 are virtual touch buttons that are floating above the display screen 350. They can be located near the corners or edges of the screen as shown. User can use cross motion (sliding "X" or "+" shape) at location 1030 on the screen 350 to close and hide the floating buttons. User can use circular motion (not shown) to bring back up the floating buttons.

Figure 11A:
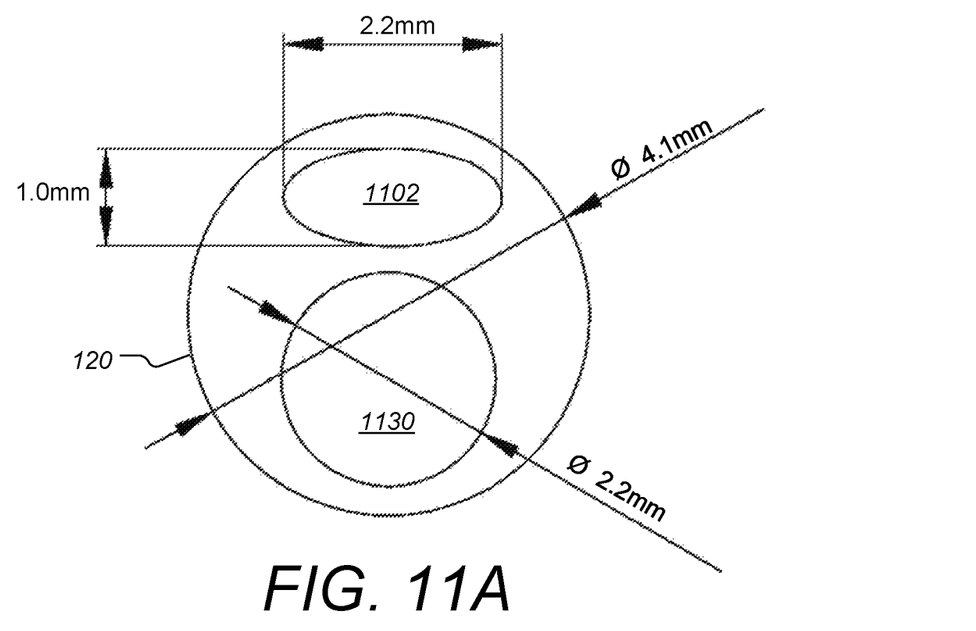
FIGS. 11A and 11B are cross sections showing further detail of a cannula and a distal tip that form part of a side-mountable disposable portion of a portable endoscope, according to some embodiments.
Figure 11B:
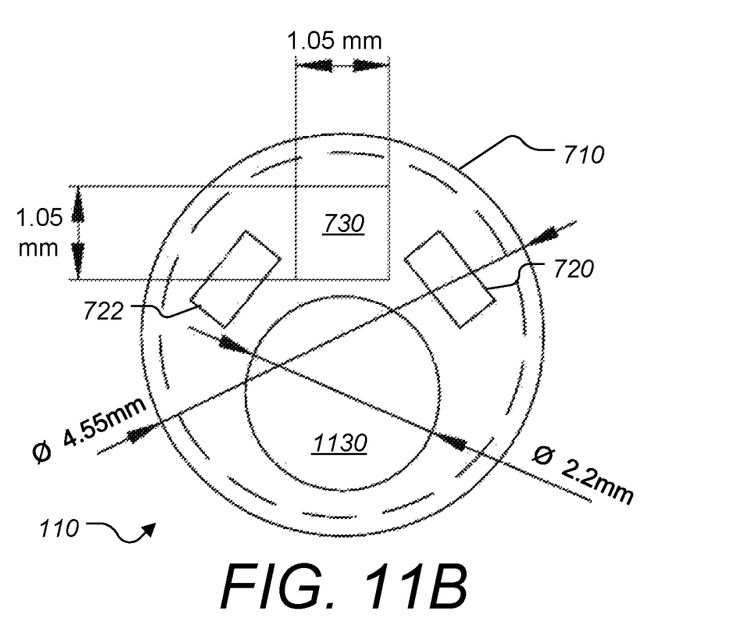

FIGS. 11A and 11B are cross sections showing further detail of a cannula and a distal tip that form part of a disposable portion of a portable endoscope, according to some embodiments. FIG. 11A shows some example dimensions for the cannula 120. Cannula 120 has an O.D. of 4.1 mm. The working channel lumen has an I.D. of 2.2. mm and the cable lumen 1102 is oval with dimensions shown. Cable lumen 1102 can be used to carry the electrical wires leading to the camera module and LEDs on distal tip 110. In FIG. 11B the dimensions and placement of camera module 730, LEDS 720 and 722 are shown. Camera module 730 can have a square area 1.05 mm per side, and each of LEDs 720 and 722 can be a rectangle with a larger side approximately the same length as a side of camera 730.

According to some embodiments, the endoscope 100 described herein can be used for gynecology applications. For example, an endometrial biopsy device, such as a Pipelle, an endometrial biopsy cannula such as the SoftFlex device offered by Integra Live Sciences Corp. of New Jersey, a device such as the EndoSampler device offered by MedGyn in Illinois, or a surgical curette, etc. can be inserted through the working channel for endometrial biopsy.

Although the foregoing has been described in some detail for purposes of clarity, it will be apparent that certain changes and modifications may be made without departing from the principles thereof. It should be noted that there are many alternative ways of implementing both the processes and apparatuses described herein. Accordingly, the present embodiments are to be considered as illustrative and not restrictive, and the body of work described herein is not to be limited to the details given herein, which may be modified within the scope and equivalents of the appended claims.

What it claimed is:

1. An endoscope comprising:
    a reusable handle having a top side, two latera sides and a bottom side and comprising:
        an elongated side slot in an intermediate portion of one of the lateral sides of said reusable handle, between the top side and the bottom side thereof, and extending in a direction along a longitudinal axis of the endoscope;
        a display module with a screen to display images;
        wherein said display module is mechanically mounted to said reusable handle for rotation and/or pivoting relative to the handle;
        signal processing circuits inside the reusable handle, operatively coupled with said display module; and
        a first electrical connector at said handle, operatively coupled to said signal processing circuits;
    a single-use, disposable portion comprising:
        an insert housing configured to releasably snap into and release from said elongated side slot in said one of the lateral sides of the reusable handle by motion relative to said handle in a direction transverse to said longitudinal axis and transverse to a direction from said top side to said bottom side of the handle;
        a cannula extending distally from the insert housing;
        wherein said cannula is configured for rotation about said longitudinal axis relative to said insert housing;
        a first lumen extending along said longitudinal axis, from a first proximal port that starts at a location proximal from both the insert housing and said handle and ends at a distal portion of the cannula;
        an imaging and illumination module at a distal portion of the cannula;
        a second electrical connector operatively coupled with said imaging and illumination module and configured to releasably mate with said first electrical connector to establish an electrical connection between said imaging and illumination module and said signal processing circuits;
    control buttons on at least one of the handle and the display module, coupled with said display module, signal processing circuits and imaging and illumination module to selectively cause the imaging and illumination module to illuminate a field of view and take images thereof and cause the display module to display said images.

2. The endoscope of claim 1, in which said side slot extends from a proximal end of the handle to a distal end of the handle.

3. The endoscope of claim 2, in which said housing, when snapped into said side slot of the handle, extends from said proximal end of the handle to said distal end of the handle.

4. The endoscope of claim 1, in which said handle comprises an outside wall of plural components sufficiently sealed against each other to enable repeated steam-sterilizing of said handle.

5. The endoscope of claim 4, further including a removable plug closing off said first electrical connector to assist in sealing the handle for said repeated steam-sterilizing.

6. The endoscope of claim 4, further comprising o-rings and/or gaskets sealing said components against each other.

7. The endoscope of claim 1, in which said first electrical connector is configured for coupling to external equipment comprising one or more of a workstation and image archiving and/or transmitting units for sending thereto images taken with said imaging and illumination module.

8. The endoscope of claim 1, further including a cable electrically coupling said second electrical connector with said imaging and illumination module, wherein said cable has a distal portion inside said cannula and a proximal portion that is outside the cannula and the housing and is sufficiently long and flexible to enable rotation of the cannula relative to the handle about said longitudinal axis of at least 180 degrees when the housing is snapped in said side slot of the handle and the first and second connectors are mated.

9. The endoscope of claim 1, further including a second proximal port extending proximally from the proximal ends of both the housing and the handle when the housing is snapped into the handle side slot.

10. The endoscope of claim 1, further including an intermediate port that is distal from said handle when said housing is snapped into the handle but is proximal from said distal portion of the cannula.

11. The endoscope of claim 1, further including a second lumen extending along said longitudinal axis and fluidly coupled with at least one port that is in addition to said first proximal port.

12. The endoscope of claim 1, in which said first port is vertically in line with a center of said display module and less than 15 cm from the center of the display module, thereby placing the first port in a line and angle of site of a viewer that includes both the display module and the first port.

13. The endoscope of claim 1, in which said handle includes a rechargeable battery in said handle, wherein said first electrical connector is coupled electrically with said battery to enable charging the battery through said first electrical connector.

14. The endoscope of claim 1, in which said signal processing circuits in the handle include WiFi circuits and further including an antenna configured to wirelessly transmit images taken with said imaging and illumination module.

* * * * *